(12) United States Patent
Bach et al.

(10) Patent No.: US 9,572,707 B2
(45) Date of Patent: Feb. 21, 2017

(54) MULTI-LAYERED ADHESIVE APPLIANCE

(71) Applicant: Coloplast A/S, Humlebaek (DK)

(72) Inventors: Anders Bach, Kobenhavn S (DK); Esben Stroebech, Hoersholm (DK); Mads Lykke, Broenshoej (DK); Astrid Toftkaer, Soeborg (DK); Hasse Buus, Humlebaek (DK); Tom Kongebo, Humlebaek (DK)

(73) Assignee: Coloplast A/S, Humlebaek (DK)

( * ) Notice: Subject to any disclaimer, the term of this patent is extended or adjusted under 35 U.S.C. 154(b) by 57 days.

(21) Appl. No.: 14/012,230

(22) Filed: Aug. 28, 2013

(65) Prior Publication Data

US 2013/0345654 A1    Dec. 26, 2013

Related U.S. Application Data

(63) Continuation of application No. 12/452,227, filed as application No. PCT/DK2008/050148 on Jun. 17, 2008, now abandoned.

(30) Foreign Application Priority Data

Jun. 19, 2007  (DK) ................................ 2007 00895
Jun. 21, 2007  (DK) ................................ 2007 00896

(Continued)

(51) Int. Cl.
*A61F 5/443*   (2006.01)
*A61F 5/445*   (2006.01)
(Continued)

(52) U.S. Cl.
CPC ............... *A61F 5/443* (2013.01); *A61F 5/445* (2013.01); *A61L 24/0031* (2013.01);
(Continued)

(58) Field of Classification Search
CPC ...................................................... A61F 5/443
(Continued)

(56) References Cited

U.S. PATENT DOCUMENTS 3,121,021 A    2/1964    Copeland
4,192,785 A    3/1980    Chen et al.
(Continued)

FOREIGN PATENT DOCUMENTS

AU    2004/227821    4/2005
AU    2004224963     5/2005
(Continued)

OTHER PUBLICATIONS

Antonio Aguilar, "A Patient Identification System using RFID and IEEE 8o2.11b Wireless Networks", Master of Science Thesis, KTH Information and Communication Technology COS/CCS 2007-13, Stockholm, Sweden 2007.

(Continued)

*Primary Examiner* — Adam Marcetich
*Assistant Examiner* — Guy K Townsend
(74) *Attorney, Agent, or Firm* — Coloplast Corp., Coloplast A/S; Nick Baumann

(57) ABSTRACT

A body waste collecting device comprising an adhesive composite that fastens a collecting bag to the skin is disclosed. The adhesive composite is highly moisture resistant while still being water absorbing. The adhesive composite comprises at least three layers, a backing layer, a moisture absorbing layer and a thin layer of vapor permeable, low-absorbing adhesive layer.

8 Claims, 1 Drawing Sheet

(30) Foreign Application Priority Data

| Jul. 6, 2007 | (DK) | 2007 01003 |
|---|---|---|
| Oct. 3, 2007 | (DK) | 2007 01424 |
| Jun. 2, 2008 | (DK) | 2008 00755 |

(51) Int. Cl.
*A61L 24/00* (2006.01)
*A61L 28/00* (2006.01)

(52) U.S. Cl.
CPC .......... *A61L 24/0073* (2013.01); *A61L 28/00* (2013.01); *A61L 2400/04* (2013.01)

(58) Field of Classification Search
USPC .................................. 604/344, 346, 363
See application file for complete search history.

(56) References Cited

U.S. PATENT DOCUMENTS

| 4,372,303 | A |  | 2/1983 | Grossmann et al. |
| 4,445,898 | A |  | 5/1984 | Jensen |
| 4,681,574 | A |  | 7/1987 | Eastman |
| 4,699,146 | A |  | 10/1987 | Sieverding |
| 4,946,720 | A |  | 8/1990 | Oishi et al. |
| 5,051,259 | A |  | 9/1991 | Olsen et al. |
| 5,423,783 | A |  | 6/1995 | Battles et al. |
| 5,545,154 | A |  | 8/1996 | Oberholtzer |
| 5,607,413 | A | * | 3/1997 | Holmberg ............ A61F 5/448 604/332 |
| 5,609,585 | A | * | 3/1997 | Botten ............ A61F 5/443 604/332 |
| 5,633,010 | A |  | 5/1997 | Chen |
| 5,643,187 | A |  | 7/1997 | Naestoft et al. |
| 6,106,507 | A | * | 8/2000 | Botten ............ A61F 5/443 604/336 |
| 6,197,010 | B1 | * | 3/2001 | Leise, Jr. ............ A61F 5/443 604/338 |
| 6,248,915 | B1 |  | 6/2001 | Ito et al. |
| 6,566,576 | B1 |  | 5/2003 | Komerska et al. |
| 6,764,474 | B2 |  | 7/2004 | Nielsen et al. |
| 7,259,190 | B2 |  | 8/2007 | Lykke |
| 7,919,182 | B2 |  | 4/2011 | Hamada et al. |
| 8,076,528 | B2 |  | 12/2011 | Lam et al. |
| 2002/0193724 | A1 |  | 12/2002 | Stebbing et al. |
| 2004/0002687 | A1 |  | 1/2004 | Burns et al. |
| 2004/0106908 | A1 |  | 6/2004 | Leise et al. |
| 2005/0065486 | A1 | * | 3/2005 | Fattman ............ A61F 5/443 604/332 |
| 2005/0074482 | A1 |  | 4/2005 | Goldman et al. |
| 2006/0029651 | A1 |  | 2/2006 | Brothers |
| 2007/0009582 | A1 | * | 1/2007 | Madsen ............ A61L 15/585 424/445 |
| 2007/0060855 | A1 |  | 3/2007 | Leung et al. |
| 2007/0185464 | A1 |  | 8/2007 | Fattman et al. |
| 2008/0311396 | A1 |  | 12/2008 | Hamada et al. |
| 2010/0015331 | A1 |  | 1/2010 | Bieser et al. |
| 2010/0191204 | A1 | * | 7/2010 | Bach ............ A61F 5/443 604/344 |
| 2010/0204664 | A1 |  | 8/2010 | Bach et al. |
| 2010/0204665 | A1 |  | 8/2010 | Stroebech et al. |
| 2010/0280429 | A1 |  | 11/2010 | Bach et al. |
| 2010/0286640 | A1 |  | 11/2010 | Nordby et al. |
| 2011/0034890 | A1 |  | 2/2011 | Stroebech et al. |
| 2011/0125115 | A1 |  | 5/2011 | Anders et al. |
| 2011/0230850 | A1 |  | 9/2011 | Stroebech et al. |

FOREIGN PATENT DOCUMENTS

| CA | 2486485 | 5/2006 |
| CN | 1313744 | 9/2001 |
| CN | 1338916 | 3/2002 |
| CN | 1803114 | 7/2006 |
| EP | 0300620 | 1/1989 |
| EP | 0437944 | 7/1991 |
| EP | 0686381 | 12/1995 |
| EP | 0880973 | 12/1998 |
| EP | 1527789 | 5/2005 |
| EP | 1 679 085 | 7/2006 |
| GB | 2085916 | 3/1982 |
| GB | 2152387 | 8/1985 |
| JP | 2004067720 | 3/2004 |
| WO | WO 02/066087 | 8/2002 |
| WO | WO 2005/021058 | 3/2005 |
| WO | WO 2005/032401 | 4/2005 |
| WO | WO 2007/082538 | 7/2007 |
| WO | WO 2007/092289 | 8/2007 |
| WO | WO 2007/128320 | 11/2007 |
| WO | WO 2008/074333 | 6/2008 |
| WO | WO 2008/154930 | 12/2008 |
| WO | WO 2009/006901 | 1/2009 |
| WO | WO 2010006600 | 1/2010 |
| WO | WO 2010/066254 | 6/2010 |

OTHER PUBLICATIONS

Kaelble, "Theory and Analysis of Peel Adhesion: Adhesive Thickness Effort", J. Adhesion 1992, v. 37, pp. 205-214.

Aherne et al. "Characterizing the viscoelastic properties of thin hydrogel-based . . . " Journal of the Royal Society, v. 2(5), Dec. 22, 2005.

"Bioflex Performance Materials". Scapa Healthcare: <http://scapahealthcare.com/Capabilities/Materials.aspx>. Mar. 2014.

* cited by examiner

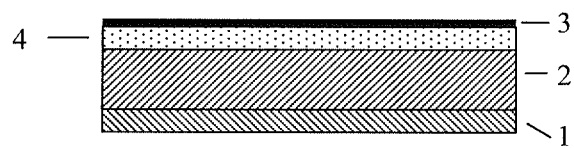

MULTI-LAYERED ADHESIVE APPLIANCE

This is a continuation of Ser. No. 12/452,227, filed, Apr. 2, 2010, which is a 371 of PCT/DK08/050148, filed Jun. 17, 2008, and which has priority of PA 2007 00895 filed Jun. 19, 2007, PA 2007 00896 filed Jun. 21, 2007, PA 2007 01003 filed Jul. 6, 2007, PA 2007 01424 filed Oct. 3, 2007, and PA 2008 00755 filed Jun. 2, 2008, the disclosures of which are incorporated herein by reference.

FIELD OF THE INVENTION

The present invention relates to an adhesive that attaches a collecting device to the human skin e.g. an ostomy device. Such adhesives need to be moisture absorbing to keep the skin dry, but absorbed moisture reduces the adhesive bonding to the skin. This invention discloses a body waste collecting device comprising an adhesive composite that maintains its adhesive properties even after considerable moisture absorption.

BACKGROUND

When designing a skin adhesive, one of the major issues is to keep the skin relatively dry underneath the adhesive so as to prevent maceration. Maceration occurs when the skin is unable to get rid of moisture from transpiration and results in degradation of the skin's barrier function as well as bad adhesion of the device to the skin.

Usually, skin adhesive keeps the skin dry by being moisture permeable. This allows moisture to transport through the adhesive from the skin side to the opposite side, where it is allowed to evaporate.

Adhesives for fastening a bodily waste collecting pouch or tube are usually covered by a moisture impermeable layer that does not allow moisture from the skin to permeate through the adhesive and out into the surroundings.

Therefore, adhesives for fastening a collecting pouch or tube are made moisture absorbent. Absorbing particles or hydrocolloids (HC) are mixed into an adhesive matrix in order to absorb moisture from the skin and thereby keeping the skin relatively dry. This technique is well known in the art and forms the basis for most commercially available ostomy adhesives see, e.g. U.S. Pat. No. 4,192,785.

The major problem in using an absorbing adhesive is that the bonding properties change as the adhesive absorbs moisture. What started out as being a well-bonded adhesive, usually ends up being a weak-bonded adhesive after absorbing moisture. This effect is particularly a problem for hydrocolloid-based adhesives. These adhesives comprise two phases, a hydrophobic matrix with hydrophilic hydrocolloids (HC) dispersed therein. As the adhesive absorbs moisture from the skin, the hydrocolloids swell and take up an increasing amount of space in the skin-bonding zone. It is the hydrophobic part of the adhesive that is responsible for the bonding to the skin and as the hydrophobic part is being "squeezed" out by the expanding hydrophilic domains, the skin bonding is reduced. There is further a risk that, if small drops of moisture, e.g. due to active perspiration (sweating) are formed between the skin and the adhesive, small parts of hydrocolloid can be washed out into the droplet and thus reducing bonding between the skin and the adhesive. This creates an area in the skin-adhesive interface where no new adhesive bond can be formed as the HC has no cohesive and adhesive power in it self. If there had been no HC present, the adhesion would be better but then there would be no absorbing capacity of the adhesive.

Hence, there is a need to isolate the absorbing part of the adhesive from the skin, and still maintain an ability to adhere and absorb moisture.

In AU 2004224963, a two-layered adhesive for ostomy and wound care applications is disclosed. The invention combines the mechanical effects of two layers of different hydrocolloid (HC) based adhesives. One layer close to the skin provides good initial tack while the other layer is 'soft' and provides good moisture resistance. The patent does not address the change in properties after moisture absorption in the layer. This moisture absorption is bound to be large if maceration of the skin is to be kept at arms length—The HO adhesive described in the patent is based on hydrophilic particles (HC) dispersed in a moisture impermeable matrix: Thus, moisture permeation can only be achieved through the particles. For moisture to permeate through the adhesive matrix, particles need to touch each other. To achieve sufficient moisture permeability, lots of particles need to touch each other and this can only be achieved by mixing in large amounts of particles. All of these particles will absorb moisture and the entire adhesive will significantly change properties when exposed to water. Further, the patent does not solve the problem of HC in the surface of the adhesive that can be washed out by active perspiration, destroying the ability of the adhesive to adhere to the skin.

In EP1679085, a skin adhesive is disclosed with very good water vapour permeability. This adhesive is in itself very low absorbing and is thus unsuitable for holding a pouch for collecting bodily waste because of the arguments mentioned above. However, because of the very good adhesive properties and the high permeability of the adhesive, it is suitable for a skin-facing layer as it does not change properties significantly when exposed to water. It can therefore be combined with an absorbing layer to yield an adhesive wafer suitable for use in attaching a pouch for collecting bodily waste.

In WO2007/092289, a number of ostomy devices containing several different layers are disclosed. A common feature of all these devices is that the skin-facing layer is liquid permeable, thus allowing liquid to transport from skin to a layer of absorbing material behind the skin facing layer. The device enclosed in the present invention, the skin-facing layer is liquid impermeable but moisture permeable. Even when the skin-facing layer only covers part of the absorbing layer, the absorbing layer is still liquid impermeable making the entire skin-facing surface liquid impermeable.

It has now surprisingly been found, that the layered construction according to the invention provides a collecting device comprising an adhesive wafer that maintains its adhesive properties even after considerable moisture absorption.

SUMMARY OF THE INVENTION

The present invention relates to a pressure sensitive adhesive wafer for fastening a body waste collecting device to the skin. The pressure sensitive adhesive wafer is a composite containing at least three layers:
 (1) A skin facing low-absorbing adhesive layer with good moisture permeability
 (2) A moisture absorbing layer.
 (3) A backing layer

BRIEF DESCRIPTION OF THE DRAWING

FIG. 1 shows an edge view of an adhesive layered construction used in a collecting device according to the invention. The adhesive composite in the FIGURE contains a moisture permeable, low-absorbing, skin-facing adhesive layer (1), an absorbing layer (2), an optional layer of polymer material (4) and a backing layer (3).

DETAILED DESCRIPTION OF THE PRESENT INVENTION

The aim of the invention is to increase the wear time of moisture absorbing adhesive wafer by moving the moisture absorption away from the skin-adhesive interface and further into the adhesive.

In an embodiment of the invention, a body waste collecting device comprising
- a collecting pouch
- an adhesive wafer for attachment to the body, comprising
  - a backing layer
  - at least one layer of absorbing material
  - a skin facing layer of a low-absorbent, liquid impermeable, moisture permeable adhesive composition By body waste collecting device is meant a device being able to collect and hold the output in a collecting item for a predefined time. The holding in place of the device may be obtained by a skin adhesive and the collection may be obtained by a bag.

In one embodiment of the invention, an adhesive composite is disclosed comprising at least two layers. The first skin-facing layer (1) has low moisture absorption capacity but can permeate moisture from skin to the second layer (2). The second layer (2) has good moisture absorption properties. Using such a construction drastically increases the peel force of the adhesive, if the skin-adhesive interface has been subjected to water.

Liquid impermeable, moisture permeable layer is a layer that does not allow liquid to penetrate through the layer, but allows moisture to permeate through the layer. This layer is meant to retain perspiration in its liquid state close to the sweat glands, but allows it to slowly diffuse through the layer into the absorbing layer.

The skin facing pressure sensitive adhesive layer must be able to transport moisture from the skin into the absorbing layer. The passive perspiration (diffusion) level of a normal inactive person is about 150 $g/m^2/24$ h [Pinnagoda, J., R. A. Tupker, T. Agner, and J. Serup. 1990. Guidelines for transepidermal water loss (TEWL) measurement. A report from the Standardization Group of the European Society of Contact Dermatitis. Contact Dermatitis 22:164-178]. Thus, the water permeability of the skin-facing layer must be able to permeate water in this order of magnitude to be able to keep skin relatively dry. The actual water permeability through the skin-facing layer is not only a function of the permeability coefficient of the skin-facing layer, but also a function of the difference in vapour pressure between the skin and the absorbing material on the other side of the skin-facing layer. A suitable way of determining the permeability of an adhesive layer is the reverse cup method disclosed herein. This method measures the water permeability of the layer with a water vapour gradient between saline water (~99% RH) and a vapour pressure of 15% RH. As the vapour pressure in the absorbing layer is presumed to be at least 15% RH, the water vapour permeability of the skin-facing layer should be at least 150 $g/m^2/24$ h as determined using the reverse cup method. The vapour pressure in the absorbing layer is usually considerably higher than the equivalent 15% RH in the reverse cup method, thus a preferred water vapour permeability of the layer is above 450 $g/m^2/24$ h and most preferred above 900 $g/m^2/24$ h.

The thin skin-facing layer should only be able to absorb a small amount of moisture in order for it to maintain its adhesive properties, when exposed to moisture. The weight gain of the pure skin-facing adhesive from its dry state to its equilibrium state with saline water should be less than 8% preferably less than 4%, determined using the method disclosed herein. Otherwise, the peel force drops too much if the adhesive absorbs moisture.

In an embodiment of the invention, the water vapour permeability of the skin facing layer of the low-absorbent, liquid impermeable, moisture permeable adhesive composition is higher than 150 $g/m^2/24$ h and the water absorption capacity is less than 8%, preferably less than 4%, as defined herein.

By low-absorbent is meant that the water absorption capacity is less than 8%, preferably less than 4%, as defined herein.

If small amounts of absorbing particles are dispersed in the pure skin-facing adhesive, the water absorption capacity of the skin facing layer should be less than 20% of the absorbing layer to maintain adhesion after water absorption.

In an embodiment of the invention, a body waste collecting device comprising
- a collecting pouch
- an adhesive wafer for attachment to the body, comprising
  - a backing layer
  - at least one layer of absorbing material
  - a skin facing layer of a low-absorbent, liquid impermeable, moisture permeable adhesive with an absorbing capacity less than 20% of the absorbing material.

The thickness of the skin-facing layer is primarily dictated by the vapour permeability of the chosen adhesive, the mechanical properties of the adhesive, the contours of the substrate (skin) and practical considerations such as ease of manufacturing. A preferred thickness of the skin-facing layer is in the range 20-500 µm.

Pressure sensitive adhesives for the thin skin-facing layer could be any hydrophobic adhesives with good vapour permeability. Such adhesives are typically adhesives that contain one or more polymers to give the adhesive cohesive strength and optionally oils and tackifier to adjust the adhesive properties.

According to one embodiment of the invention, the skin facing layer of the low-absorbent, liquid impermeable, moisture permeable adhesive composition comprising a permeable polymer selected from the group of but not limited to polypropyleneoxide, polyurethane, ethylene vinyl acetate, silicone, polyacrylate, and mixtures thereof.

As used herein a moisture permeable polymer means a polymer that absorbs less than 5% in wt, preferably less than 1%, at equilibrium and has a moisture vapour transmission rate of greater than 100 $g/m^2/24$ hrs, preferably greater than 200 $g/m^2/24$ hrs.

In one embodiment of the invention, the skin-facing pressure sensitive adhesive is crosslinked.

As used herein a crosslink means a small region in a macromolecule (polymer chain structure) from which more than 2 chains emanate. The linking may be covalent, physical or ionic.

In another embodiment of the invention, the skin-facing pressure sensitive adhesive comprises a block copolymer.

As used herein a block copolymer means a copolymer in which the repeating units in the main chain occur in blocks, eg, -(a)m-(b)n-(a)p-(b)q-, where a and b represent the repeating units and m, n, p, q, are numbers.

In a preferred embodiment of the invention, the skin-facing pressure sensitive adhesive comprises polypropyleneoxide.

In a preferred embodiment of the invention, the skin-facing pressure sensitive adhesive comprises polyurethane.

In a preferred embodiment of the invention, the skin-facing pressure sensitive adhesive comprises ethylene vinyl acetate.

The adhesive composition comprising ethylene vinyl acetate may suitably be an adhesive known in the art such as the adhesive composition disclosed, for example in Danish patent application PA 2007 01003.

In a preferred embodiment of the invention, the skin-facing pressure sensitive adhesive comprises silicone.

In a preferred embodiment of the invention, the skin-facing pressure sensitive adhesive comprises polyacrylate.

To accommodate at least the passive perspiration of 150 $g/m^2/24$ h, a layer of absorbing material of 1 mm thickness (~1000 $g/m^2$) would have to be able to absorb about 15% of its own weight over 24 h to absorb an equivalent amount of 150 $g/m^2/24$ h. The water absorption capability of the absorbing material after 24 hours should therefore be larger than 15%, as measured using the method disclosed herein. Preferably, the water absorption capability should be larger than 30% to achieve absorption of active perspiration (sweating).

In one embodiment of the invention, the layer of absorbing material is an absorbing adhesive layer.

It is preferred that the water absorbing adhesive layer have mechanical damping properties to further assist the adhesion of the skin-facing water permeable adhesive layer. The soft and mechanically damping properties of the layer is in fact what makes it an adhesive and can be quantified using DMA (Dynamical Mechanical Analysis). Here, we define an adhesive as a material that has a modulus of $G^*<330$ kPa (Dahlquist criterion) and a damping of tan $\delta>0.4$ both measured at 1 Hz. Preferred softness of the absorbing adhesive is $G^*$ less than 50 kPa at 1 hz. The parameters $G^*$ and tan $\delta$ are defined in "Dynamics of polymeric liquids", Vol 1, sec ed 1987, Bird, Armstrong and Hassager, John Wiley and Sons inc.

According to another embodiment, the layer of absorbing material comprises a soft non-adhesive material. Suitable materials include hydrophobic gels with absorbing particles, soft hydrophobic foams and other soft materials. By soft is meant materials with a modulus less than about $G^*<500$ kPa at 1 Hz.

According to a further embodiment, the layer of absorbing material is pliable, i.e. a non-memory putty-like material. By a non-memory putty-like material is meant a material having a Strain Recovery below 45% when measured as described below. More preferred the Strain Recovery for the material is below 40%, or even more preferred below 35%.

During use, an adhesive device is often subjected to excess moisture from the back or from the side, e.g. output from a stoma attacks the inner hole in the device (erosion), and the outer rim is challenged when showering or swimming. To avoid excess swelling and potential failure of the device it is often preferred that the absorbing layer does not have a too high absorption speed. It is generally preferred that the maximum absorption speed is lower than 10.000 $g/m^2/day$, preferably less than 5.000 $g/m^2/day$ and some times as low as 2000 or even 1000 $g/m^2/day$.

According to an embodiment of the invention, the skin-facing layer of the low-absorbent, liquid impermeable, moisture permeable adhesive composition covers the entire skin-facing surface of the adhesive wafer.

Optionally, the skin-facing layer only covers a part of the absorbing adhesive layer.

According to another embodiment of the invention, the skin facing layer of the low-absorbent, liquid impermeable, moisture permeable adhesive composition covers partly the skin-facing surface of the adhesive wafer.

In a preferred embodiment of the invention, the skin-facing layer of the low-absorbent, liquid impermeable, moisture permeable adhesive composition covers at least 75% of the skin facing surface of the adhesive wafer.

It may be advantageous that the absorbing layer comprises absorbent particles. According to an embodiment of the invention the absorbing layer comprising absorbent particles.

The particles may be absorbent articles such as salts, hydrocolloids, microcolloids or super absorbers in order for the layer to absorb moisture from skin.

Preferred particle size of the absorbent particles is smaller particles, as they are more difficult to see by the naked eye and will give products that are more pleasing to the eye. An upper limit on particle size is the size of the smallest dimension of the absorbing layer. Thus, a 300 μm thick absorbing layer should not contain particles with diameters above 300 μm. There is a tendency of the hygroscopic particles to agglomerate and this effect will increase with decreasing particle size. Therefore, a preferred particle size would be from 10-300 μm. Also, the particles may contain an anti agglomerating agent to reduce agglomeration of small particles.

Microcolloid particles are well known in the art e.g. from International Patent Application No. WO 02/066087, which discloses adhesive compositions comprising microcolloid particles. The microcolloid particles may have a particle size of less than 20 microns.

The absorbing layer may comprise 1-40% w/w of hydrocolloid (HC) or super absorbent particles (SAP) particles, more preferred 5-30% w/w particles.

Salt may be advantageous to use as absorber in the device of this invention. A salt like sodium chloride have an equilibrium vapour pressure of about 75% RH at skin temperature and will absorb water from skin and output because of the difference in vapour pressure.

In an embodiment of the invention, the absorbing layer comprises particles of mineral salt. The salt may be present in an amount of 1-50% w/w, more preferred in an amount of 5-25%.

The salt can be an inorganic salt or an organic salt.

According to one embodiment of the invention, the absorbing layer comprises water soluble inorganic salt from the group of but not limited to NaCl, $CaCl_2$, $K_2SO_4$, $NaHCO_3$, $Na_2CO_3$, KCl, NaBr, NaI, KI, $NH_4Cl$, $AlCl_3$ and mixtures thereof, preferably NaCl.

According to another embodiment of the invention, the absorbing layer comprises water soluble organic salt from the group of but not limited to $CH_3COONa$, $CH_3COOK$, HCOONa, HCOOK and mixtures thereof.

Preferably, the low-absorbing skin-facing adhesive and the hydrophobic matrix of the absorbing layer are identical or close to identical in composition to prevent migration of species between the two layers.

According to an embodiment of the invention, the absorbing layer is based on the same type of polymer ingredients as the permeable adhesive composition used in the skin facing layer. This way, the ingredients of the absorbing layer may be selected from the group of but not limited to polypropyleneoxide, polyurethane, ethylene vinyl acetate, silicone, polyacrylate and mixtures thereof, optionally made absorbing by adding particles.

The backing layer of the device of the present invention is preferably in the form of a polymer film, coating, laminate, textile or non-woven. The backing layer is preferably a highly flexible film, being strong enough for attachment of e.g. couplings and/or pouch and for removing the device in one piece, but soft enough to follow the movements of the body.

In one embodiment, the backing layer is a polyurethane film optionally a laminate or a coextruded film.

Preferably, the backing layer has thermoplastic elements that enable welding of e.g. a pouch or coupling ring to the adhesive wafer. Preferred thickness of the backing layer is between 15-60 μm in order to maintain the softness of the adhesive wafer.

In one embodiment of the invention, the backing layer is non-vapour permeable.

According to another embodiment, the backing layer is a multi layer film. Each layer in the film gives special properties to the backing layer. A thin weldable layer ensures good joining to the bag or coupling and a thicker soft layer ensures the mechanical properties.

According to another embodiment, the backing layer is a foam where the thickness is in between 15 and 200 my. A suitable foam backing layer is e.g. a polyethylene foam, a ethylenvinyle acetate foam, a polyurethane foam, a polyalkylene oxide and/or polyakylene oxide siloxane foam.

According to an embodiment of the invention, the adhesive wafer comprises an optional layer comprising polymer material in order to adjust the mechanical properties of the adhesive wafer. Such a layer could be composed of, but not limited to, the hydrophobic part of a hydrocolloid adhesive.

A wafer according to the invention is optionally covered in part or fully by one or more release liners, or cover films to be removed before or during application. A protective cover or release liner may for instance be siliconised paper. It does not need to have the same contour as the wafer. The release liner may be of any material known to be useful as a release liner for medical devices.

According to an embodiment of the invention, the collecting pouch is detachable.

According to another embodiment of the invention, the collecting pouch is integrated with the wafer.

The collecting pouch may be detachable from the adhesive wafer by a coupling system or the pouch and the wafer may be integrated with the wafer, e.g. by welding. The two versions are known as one piece or two-piece appliances for ostomy.

According to an embodiment of the invention, the adhesive wafer is provided with an aperture for receiving a stoma.

In order to avoid rolling up of the edge portion during wear, it may be advantageous to bevel the edge portion of the wafer.

Flexibility in the adhesive part of a medical device is often achieved by device design, such as beveling or patterning in the adhesive.

By the skin-facing surface of the adhesive is meant the side adhering to the skin.

By the pouch-facing surface or non-skin-facing surface is meant the side of the adhesive or backing pointing away from the skin (non-bonding side).

In another embodiment, the skin-facing layer and the absorbing layer is formed as a gradient in absorbing particles in the direction perpendicular to the skin surface the wafer is supposed to be attached to. For example NaCl particles in a pre-cured adhesive could be allowed to settle before the adhesive was cured. The settling will result in higher particle concentration at the bottom than at the top of the adhesive wafer, without introducing multiple layers in the adhesive. This way, the adhesive wafer construction is composed of one layer of an absorbing permeable adhesive where the particle concentration of the skin-facing side is at least 2 times lower, preferably at least 4 times lower, than the particle concentrations on the non-skin-facing side of the adhesive.

This particle gradient adhesive construction ensures that the adhesive properties are maintained during use on the skin facing side and that the absorption capacity for a healthy skin environment on the non-skin-facing side of the adhesive is obtained.

The first 10% of the skin-facing side of the total adhesive thickness defines the skin-facing side particle concentration. The first 10% of the opposite side of the adhesive (the non-skin-facing side) defines the non-skin-facing side particle concentration.

In a preferred embodiment the absorbing particles are salt particles dispersed across the adhesive thickness with a concentration of 3% w/w salt at the skin-facing side and 20% w/w at the non-skin-facing side.

According to an embodiment of the invention, the collecting device is an ostomy appliance.

According to another embodiment of the invention, the collecting device is a faecal collecting device.

According to another embodiment of the invention, the collecting device is a fistula collecting device.

Experimental Part

Methods

Determination of Water Absorption

In order to get better correlation between measured water absorption and actual performance in a humanlike environment, a modified version of the ISO 62 standard was used: Pieces of adhesive of 1×25×25 mm$^3$ were fastened on a piece of glass using double sided adhesive and the constructs were immersed in saline water (0.9% NaCl in dematerialised water) at 32° C. After 24 hours, the samples were removed and carefully dripped dry and weighed. The change in weight was recorded and reported as weight gain in percent of the original dry weight of the adhesive. In the following, we will call this value $w_{24h}$ Determination of Moisture Vapour Transmission Rate (MVTR)

MVTR was measured in grams per square meter (g/m$^2$) over a 24 hour period using an inverted Paddington cup method (British Pharmacopoeia, 1993, Addendum 1996, page 1943. HMSO London): A container or cup being water and water vapour impermeable having an opening was used. 20 ml saline water (0.9% NaCl in demineralised water) was placed in the container and the opening was sealed with the test adhesive film. The container, with a duplicate, was placed into an electrically heated humidity cabinet and the container or cup was placed up side down in a way that the water was in contact with the adhesive. The cabinet was maintained at 37° C. and 15% relative humidity (RH). After about an hour, the containers were considered to be in equilibrium with the surroundings and were weighed. 24 hours after the first weighing, the containers were weighed again. The difference in weight was due to evaporation of vapour transmitted through the adhesive film. This difference was used to calculate moisture vapour transmission rate or MVTR. MVTR was calculated as the weight loss after 24 hours divided by the area of the opening in the cup (g/m$^2$/24 h). If the adhesive film could not support the weight of the water, a supporting film with very high permeability was used as support.

Peel

Peel measurements were performed in an Instron at 300 mm/min and 90° angle. Peel strips were 25 mm wide and 100 mm long. Measured force was recorded during peel and reported peel force is an average of the peel force without end effects. Peel force is reported in N/25 mm.

Strain Recovery

A plate of the adhesive material to be tested was pressed into a plate of 1 mm thickness. From this a round sample of 25 mm in diameter was cut out and placed in a RheoStress RS600 rheometer from Thermo Electron. The geometry applied was parallel 25 mm plates. The measurement was carried out at 32° C.

A shear deformation ($\gamma$) of 15% and 5% (total 20%) was applied in two steps in order to avoid overshoot in deformation and the 20% deformation was held for 60 seconds, (the overshoot of the deformation should not exceed 22%). The total time of the deformation should be less than 90 seconds. The stress was removed and the remaining elastic forces recovered some of the applied deformation. The resulting recovery of the deformation was measured after 1000 seconds.

The Strain Recovery was defined as the percentage recovery from large step strain and was calculated as follows:
Strain Recovery=$\gamma-\gamma_{1000}/\gamma$ where $\gamma$ was 0.20 and gamma$_{1000}$ was the shear deformation after 1000 seconds, which may be seen from the curve provided by the rheometer.

Materials

The following materials were used to prepare pressure sensitive adhesives according to the invention and pressure sensitive adhesive compositions for comparison:

ACX003, allyl-terminated polyether (poly propylene oxide) viscosity 16 Pa·s from Kaneka.

Platinum catalyst, Pt-VTS. Pt-VTS is Pt-divinyl teteramethyl disiloxane in IPA (Pt 3.0 wt %).

CR600, poly-alkyl hydrogen siloxane curing agents available from Kaneka.

Aquasorb A500 Hydrocolloid from Hercules

Backing layer—PU film: BL9601, Intellicoat.

Releaseliner

Results

Two adhesive samples were prepared: First 150 g of adhesive base was prepared containing polymer, crosslinker and catalyst in ratios given in table 1.

TABLE 1

Mixing ratios of PPO adhesive base

| | wt % |
|---|---|
| Polymer AC003 | 96.45 |
| Cross linker CR600 | 3.45 |
| Catalyst | 0.10 |

10 g of this adhesive was coated on a release liner in 100 μm thickness and put in an oven to cure. 20 g of adhesive were pressed between two release liners to a 1 mm thick sheet and cured at 100° C. for 1 hour. This sample is called Sample 1. 100 g of the remaining adhesive base was mixed with 25 g Aquasorb A500 Hydrocolloid (HC) such that the total content of HC was 20%. Now, two adhesives were prepared:

Adhesive 1:

25 g of the HC containing adhesive base was placed on the backing film, a release liner was placed on top and the sandwich was placed in a 100° C. hot press with a distance between the two hot plates such that the adhesive was 1000 μm.

Adhesive 2:

20 g of the HC containing adhesive base was placed on the backing film, and the release liner with the 100 μm thick adhesive layer from step 1 was placed on top and the sandwich was placed in a 100° C. hot press with a distance between the two hot plates such that two adhesive layers had a total thickness of 1000 μm.

Adhesive 1 and 2 and sample 1 were placed in an oven at 100° C. for 30 min to post cure. Now, adhesive 1 contained one layer of adhesive between PU backing film and release liner while adhesive 2 had two adhesive layers between release liner and PU backing film—one layer of absorbing adhesive on the PU side and one layer of low-absorbing adhesive facing the release liner (skin-facing side). The low-absorbing layer was 100 μm thick.

Water absorption of Adhesive 1 and 2 and Sample 1

Water absorption experiments were performed according to the test method disclosed herein.

Dry Peel

Peel strips were cut from the two adhesive sheets. Strips were placed on the forearm of a volunteer and peeled 5 minutes after application of the strips.

Wet Peel

Peel strips were cut from the two adhesive sheets. The strips were placed in saline water for 15 min, afterwards, the adhesive was taken out of the water and excess water was quickly drip-dried. Now, the adhesives were placed on the forearm of a volunteer and given 5 min to relax, after this waiting time the strips were peeled.

MVTR

A part of the thin layer was transferred to PU backing and MVTR of the layers was tested and found to be 1800 g/m$^2$/24 h. MVTR of the PU backing alone was about 10000 g/m$^2$/24 h and is therefore negligible compared to the adhesive layer. MVTR of the 100 μm adhesive film is therefore close to 1800 g/m$^2$/24 h.

Results:

TABLE 2

Results for adhesives with and without low absorbing adhesive layer

| | Water absorption of skin-facing layer | Water absorption of absorbing layer | Water absorption of adhesive composite | Dry Av. Peel force [N/25 mm] | Wet Av. Peel force [N/25 mm] |
|---|---|---|---|---|---|
| Adh. 1 | $w_{24\,h}$ = 48% | $w_{24\,h}$ = 48% | $w_{24\,h}$ = 48% | 3.2 | 0.3 |
| Adh. 2 | $w_{24\,h}$ = 3% | $w_{24\,h}$ = 48% | $w_{24\,h}$ = 28% | 3.5 | 1.2 |

The results show that by adding a low-absorbing layer of adhesive on the skin facing side of the absorbing adhesive; the water absorption capacity has been reduced by a 40%. The dry peel force is almost unaffected by the extra layer, but the wet peel force is 300% higher than the adhesive without the layer. Thus, the absorbing adhesive had considerably better ability to stay in place when the layer of low-absorbing adhesive was coated on the skin-facing side of the adhesive, while good moisture absorption properties were maintained.

The invention claimed is:

1. A body waste collecting device comprising
a collecting pouch;
an adhesive wafer for attachment to the body, comprising at least
 a backing layer; and
 a single layer of absorbing, liquid impermeable, moisture permeable adhesive composition with a gradient of absorbing particles, the single layer of adhesive composition having a thickness and being characterized in that an absorbing salt particle concentration of a skin facing side of the single layer of adhesive compositions ranges from 2 times to 6.67 times lower than an absorbing salt particle concentration on a non-skin facing side of the single layer of adhesive composition, the skin facing side of the single layer of adhesive being defined as a first 10% of the thickness of the single layer of adhesive composition, and the non-skin facing side of the single layer of adhesive being defined as a first 10% of the thickness the single layer of adhesive composition on a side of the adhesive composition opposite the skin facing side.

2. The collecting device according to claim 1, wherein a water absorption capacity of the layer of liquid impermeable, moisture permeable adhesive composition is less than 5 wt. %.

3. The collecting device according to claim 1, wherein the layer of liquid impermeable, moisture permeable adhesive composition comprises a permeable polymer selected from the group of polypropyleneoxide, polyurethane, ethylene vinyl acetate, silicone, polyacrylate, and mixtures thereof.

4. The collecting device according to claim 1, wherein the absorbent particles NaCl particles.

5. The collecting device according to claim 1, wherein the collecting device is an ostomy appliance.

6. The collecting device according to claim 1, wherein the collecting device is a faecal collecting device.

7. The collecting device according to claim 1, wherein the collecting device is a fistula collecting device.

8. A body waste collecting device comprising:
a collecting pouch; and
an adhesive wafer for attachment of the collecting pouch to the body, the adhesive wafer including;
 a backing layer; and
 an adhesive layer having a first side disposed on the backing layer and a second skin-facing side opposite from the first side, with the adhesive layer having a thickness and provided as a single layer of a liquid absorbing and moisture permeable adhesive composition having a gradient of absorbing salt particles;
wherein the gradient of absorbing particles includes a particle concentration in a first 10% of the thickness measured on a second skin-facing side of the adhesive layer that ranges from 2 times to 6.67 times lower than the particle concentration in the first 10% of the thickness measured on the first side of the adhesive layer that is disposed on the backing layer to provide the first side of the adhesive layer with a higher absorption capacity than the second skin-facing side of the adhesive layer.

* * * * *